(12) United States Patent
Wales et al.

(10) Patent No.: US 11,730,344 B2
(45) Date of Patent: Aug. 22, 2023

(54) DEVICES AND METHODS FOR DELIVERY OF MEDICAL TOOLS

(71) Applicant: Boston Scientific Scimed, Inc., Maple Grove, MN (US)

(72) Inventors: Ryan Wales, Northborough, MA (US); Paul Smith, Smithfield, RI (US); Scott Brechbiel, Acton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 184 days.

(21) Appl. No.: 17/012,298

(22) Filed: Sep. 4, 2020

(65) Prior Publication Data

US 2020/0397231 A1 Dec. 24, 2020

Related U.S. Application Data

(63) Continuation of application No. 15/639,212, filed on Jun. 30, 2017, now Pat. No. 10,791,911.

(Continued)

(51) Int. Cl.
*A61B 1/00* (2006.01)
*A61B 1/018* (2006.01)
*A61B 17/128* (2006.01)
*A61B 17/00* (2006.01)
*A61B 17/122* (2006.01)

(52) U.S. Cl.
CPC ........ *A61B 1/00098* (2013.01); *A61B 1/0014* (2013.01); *A61B 1/00089* (2013.01); *A61B 1/00101* (2013.01); *A61B 1/00135* (2013.01); *A61B 1/00137* (2013.01); *A61B 1/018* (2013.01); *A61B 17/00234* (2013.01); *A61B 17/1285* (2013.01); *A61B 1/00073* (2013.01); *A61B 17/122* (2013.01); *A61B 2017/0034* (2013.01); *A61B 2017/00269* (2013.01); *A61B 2017/00296* (2013.01);

(Continued)

(58) Field of Classification Search
CPC .............. A61B 1/0008; A61B 1/00089; A61B 1/00137; A61B 1/0014
See application file for complete search history.

(56) References Cited

U.S. PATENT DOCUMENTS

| 5,897,487 A | 4/1999 | Ouchi |
| 5,913,865 A | 6/1999 | Fortier et al. |

(Continued)

FOREIGN PATENT DOCUMENTS

| CN | 202005582 U | 10/2011 |
| CN | 102834042 | 12/2012 |

(Continued)

OTHER PUBLICATIONS

Chinese Office Action in corresponding Chinese Application No. 201780040270.7, dated Mar. 26, 2021 (6 pages).

(Continued)

*Primary Examiner* — Aaron B Fairchild
(74) *Attorney, Agent, or Firm* — Bookoff McAndrews, PLLC (57) ABSTRACT

An endoscopic cap assembly may include a sleeve and a cap. The cap may include a cap channel extending along an external surface of the cap. The cap may also include an engagement feature extending radially outwardly from the external surface of the cap.

20 Claims, 9 Drawing Sheets

Related U.S. Application Data (60) Provisional application No. 62/357,596, filed on Jul. 1, 2016.

(52) U.S. Cl.
CPC ............ *A61B 2017/00349* (2013.01); *A61B 2017/00358* (2013.01); *A61B 2017/00477* (2013.01)

(56) References Cited

U.S. PATENT DOCUMENTS

| | | | |
|---|---|---|---|
| 7,815,565 B2 | 10/2010 | Stefanchik et al. | |
| 2001/0053909 A1 | 12/2001 | Nakada et al. | |
| 2003/0009085 A1 | 1/2003 | Arai et al. | |
| 2004/0210111 A1 | 10/2004 | Okada | |
| 2005/0033115 A1 | 2/2005 | Okada | |
| 2005/0049455 A1 | 3/2005 | Ootawara et al. | |
| 2008/0177135 A1 | 7/2008 | Muyari et al. | |
| 2008/0188869 A1 | 8/2008 | Weitzner et al. | |
| 2008/0188890 A1* | 8/2008 | Weitzner | A61B 1/04 606/205 |
| 2008/0215064 A1 | 9/2008 | Motosugi | |
| 2008/0281299 A1 | 11/2008 | Menn | |
| 2010/0113878 A1 | 5/2010 | Kawano | |
| 2011/0152616 A1 | 6/2011 | Deal | |
| 2011/0152618 A1* | 6/2011 | Surti | A61B 1/0008 600/129 |
| 2011/0257477 A1* | 10/2011 | McWeeney | A61B 1/31 600/104 |
| 2013/0090527 A1* | 4/2013 | Axon | A61B 1/0008 600/114 |
| 2013/0274766 A1 | 10/2013 | Isaacson et al. | |
| 2014/0213847 A1 | 7/2014 | Green et al. | |
| 2019/0261835 A1* | 8/2019 | Ostrovsky | A61B 1/00112 |

FOREIGN PATENT DOCUMENTS

| | | |
|---|---|---|
| CN | 105011710 A | 11/2015 |
| CN | 105212981 | 1/2016 |
| JP | H08 131397 | 5/1996 |
| JP | H0966019 | 3/1997 |
| JP | 2003204919 A | 7/2003 |
| JP | 2005131435 A | 5/2005 |
| JP | 2008253597 A | 10/2008 |
| JP | 2010022697 A | 2/2010 |
| JP | 2011030764 A | 2/2011 |
| JP | 2015186534 A | 10/2015 |

OTHER PUBLICATIONS

Office Action in Japanese Patent Application No. 2018-562344, dated May 11, 2021 (3 pages).

Office Action in Japanese Patent Application No. 2021-163563, dated Oct. 11, 2022 (3 pages).

* cited by examiner

DEVICES AND METHODS FOR DELIVERY OF MEDICAL TOOLS

CROSS-REFERENCE TO RELATED APPLICATIONS

This patent application claims the benefit of priority of U.S. patent application Ser. No. 15/639,212, filed Jun. 30, 2017, which claims the benefit of priority under 35 U.S.C. § 119 to U.S. Provisional Patent Application No. 62/357,596, filed Jul. 1, 2016, each of which is herein incorporated by reference in its entirety.

TECHNICAL FIELD

Various aspects of the present disclosure relate generally to a cap assembly for an insertion device and related methods. More specifically, the present disclosure relates to a cap assembly having one or more features for selectively engaging a medical tool, and methods of the same.

BACKGROUND

Insertion devices, such as, e.g., an endoscope, may provide a visual image of the internal anatomy of a subject while one or more medical tools are manipulated to perform a selected medical procedure. For instance, in endoscopic submucosal dissection (ESD) procedures, an endoscope is delivered through a subject's gastrointestinal (GI) tract (or through an incision) to a location within the subject. Once positioned within the subject, a needle or other such fluid injection device may be delivered through a working channel of the endoscope to facilitate lifting a lesion or other such tissue abnormality from surrounding tissue portions of the subject. Once lifted, the lesion may be partially resected (e.g., cut) via a knife, blade, or other such tool delivered through the working channel. Due to the difficulty in gaining a clear visual image of the lesion during resection, a hemoclip (e.g., the Resolution™ Clip sold by Boston Scientific) may be placed on the partially-resected lesion.

Next, tape or other such means may be used to cover the tip of a snare in a sheath so as to avoid mucosal injury. The covered snare is delivered through the body of the subject, externally of the endoscope (e.g., through the nose of the subject) and a forceps or grasper device is delivered through the working channel of the endoscope. The tape on the snare then may be at least partially removed or peeled back to expose the snare loop using the forceps. Next, the forceps may be used to guide the snare loop about the hemoclip and an operator may close the snare loop around (e.g., lasso) the hemoclip. Due to the relative stiffness of the snare, an operator may manipulate (e.g., push, pull, lift, etc.) the snare, and consequently, the hemoclip to re-orient the partially-resected lesion to enable increased visibility and access to the submucosa. However, delivery of the snare externally of the endoscope and forceps through the endoscope, approximating the forceps towards the snare, and then positioning the snare about the hemoclip may be challenging, tedious, and time consuming, which may increase medical costs associated with such procedures.

The systems, devices, and methods of the current disclosure may rectify some of the deficiencies described above or address other aspects of the prior art.

SUMMARY

Embodiments of the present disclosure relate to, among other things, a cap assembly having one or more features for selectively engaging a medical tool. Each of the embodiments disclosed herein may include one or more of the features described in connection with any of the other disclosed embodiments.

In one arrangement, an endoscopic cap assembly may include a sleeve and a cap. The cap may include a cap channel extending along an external surface of the cap. The cap may also include an engagement feature extending radially outwardly from the external surface of the cap.

The endoscopic cap may include one or more of the following features. The engagement feature may comprise a protrusion having a post and a head. The head may have a cross-sectional dimension larger than a cross-sectional dimension of the post. The sleeve may have a varied outer dimension along a length of the sleeve. The engagement feature may be positioned distally of the cap channel. The cap channel may have a first depth at a first location along the cap channel and a second depth at a second location along the cap channel. The second location may be closer to the engagement feature than the first location, and the second depth may be less than the first depth. The cap may have a proximal end having a first outer dimension, and the cap may have a distal end having a second outer dimension, smaller than the first outer dimension. The cap may comprise a transparent material. The cap may include a drain hole extending through a side wall of the cap. The sleeve may include a sleeve channel extending along an external surface of the sleeve. The sleeve channel may be aligned with the cap channel. The sleeve may include a pair of arms. The arms may be positioned distally of the sleeve channel and aligned with the cap channel.

In another arrangement, an endoscopic system may include an endoscope, and a cap assembly coupled to the endoscope. The cap assembly may include an elastomeric sleeve and a cap having a medical tool engagement feature. The endoscopic system may also include a medical tool including a sheath and a snare loop. In a first arrangement, the snare loop may be positioned around the engagement feature.

The endoscopic system may include one or more of the following features. The cap may further include a cap channel extending along a length of the cap, and in the first arrangement, the sheath may be received within the cap channel. The sleeve may further include a sleeve channel extending along a length of the sleeve, and the sleeve channel may be aligned with the cap channel. The sleeve may further include a pair of arms, and in the first arrangement, the sheath may be received within the arms of the sleeve. In a second position, the snare loop may be expanded and positioned distally of the first position.

A method may include engaging a snare loop of a medical tool around an engagement feature of an endoscopic cap coupled to an endoscope. The method may also include delivering the endoscope to a location within a subject and placing a hemoclip onto a tissue abnormality within the subject. Further, the method may include expanding the snare loop and disengaging the snare loop from the engagement feature. Also, the method may include tightening the snare loop about the hemoclip.

The method may further include one or more of the following features. Delivering the endoscope may include delivering the endoscope while the snare loop is tightened about the engagement feature. The method may further include extending the snare loop distally of the engagement feature at an angle relative to a central longitudinal axis of the endoscopic cap.

It may be understood that both the foregoing general description and the following detailed description are exemplary and explanatory only and are not restrictive of the invention, as claimed.

As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal."

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DETAILED DESCRIPTION

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical tool or insertion device. When used herein, "proximal" refers to a position relatively closer to the exterior of the body or closer to a medical professional using the medical tool or insertion device. In contrast, "distal" refers to a position relatively further away from the medical professional using the medical tool or insertion device, or closer to the interior of the body.

Figure 1:
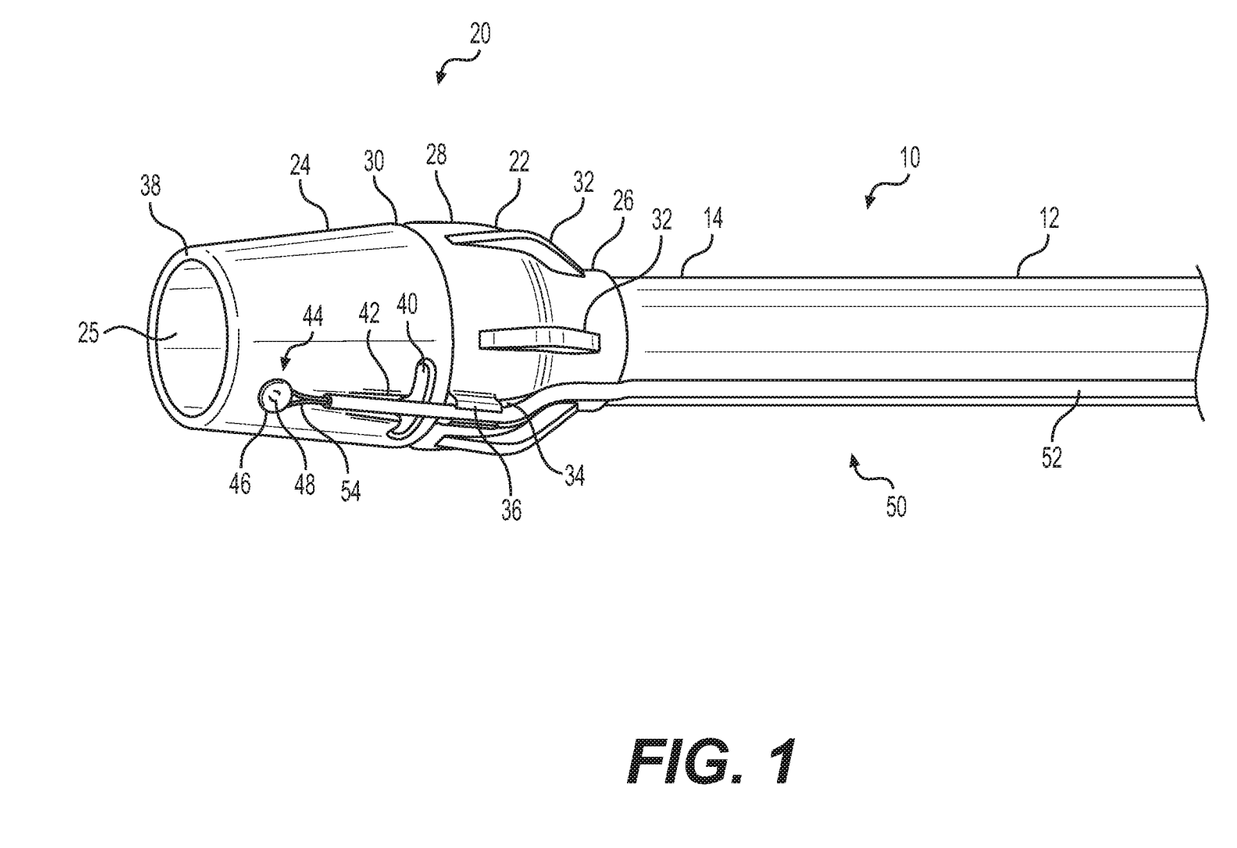
FIG. 1 illustrates an exemplary cap assembly coupled to an exemplary endoscope and medical tool.

FIG. 1 illustrates an exemplary endoscope 10. Endoscope 10 may include any device configured to allow a medical professional to perform medical diagnoses and/or treatments on a subject. For example, endoscope 10 may include any device configured to allow a user to access and view internal areas of a subject's body. Additionally or alternatively endoscope 10 may itself be a medical tool and/or include any device configured to deliver medical tools, such as, for example, biopsy forceps, graspers, baskets, snares, probes, scissors, retrieval devices, lasers, and/or other tools, into a subject's body. Endoscope 10 may be inserted into any one of a variety of body openings, lumens, and/or cavities, e.g., a gastrointestinal lumen.

Endoscope 10 may be a sterile, single-use, and disposable endoscope 10. Alternatively, endoscope 10 may be a multiple-use, non-disposable endoscope 10. Endoscope 10 may include any of a ureteroscope, a hysteroscope, a uteroscope, a bronchoscope, a cystoscope, and similar devices. Such devices may be single-use and disposable, or multiple-use and non-disposable.

Endoscope 10 may include a handle (not shown) at a proximal end thereof. The handle may have any shape suitable for gripping and controlling features of endoscope 10. For example, the handle may have an ergonomic shape designed to be held comfortably in the hand, e.g., the palm of the hand. Endoscope 10 may include a shaft 12 extending from a proximal end (not shown) coupled to (e.g., detachably or permanently connected to) the handle towards a distal end 14. Endoscope 10 may include a steering mechanism (not shown) for deflecting shaft 12 along one or more planes. For example, the handle may include an actuator (not shown) coupled to one or more portions of shaft 12 at or near distal end 14 of shaft 12 via one or more control members, such as steering wires (not shown). Any suitable steering mechanism and/or actuators (e.g., wheel, slider, trigger, button, joystick, etc.) may be used. According to some aspects, the actuator may include a locking device (not shown), such that the actuator may be locked in place when distal end 14 of shaft 12 is in a desired position.

Shaft 12 may include at least one working channel 16 (FIGS. 5A, 6A-6C, 7A-7C, and 8) extending between the proximal end of shaft 12 and distal end 14 of shaft 12. While only a single working channel 16 is depicted, e.g., in FIGS. 5A, 6A-6C, 7A-7C, and 8, such a depiction is merely exemplary. For example, working channel 16 may be a primary working channel 16 for delivery of one or more medical tools, as will be described in further detail below. Shaft 12 may, however, include additional channels (not shown) extending between the proximal end and distal end 14 of shaft 12. Such additional channels may have different shapes and/or sizes. For example, working channel 16 may have a first cross-sectional size (e.g., diameter) or first shape (e.g., circular, ovular, etc.) while one or more additional channels may have a second cross-sectional size (e.g., diameter) or second shape (e.g., circular, ovular, etc.) different than the first size and first shape. In some examples, shaft 12 may include one or more electronic components, such as a camera or other imaging device, a light source, and/or other sensor (not shown). Additionally or alternatively, one of the additional channels may provide a lumen for light delivery and/or steering control members (not shown) associated with the actuator for steering shaft 12.

Distal end 14 of shaft 12 may be coupled to a cap assembly 20 to facilitate various medical procedures, e.g., endoscopic submucosal dissection (ESD). Cap assembly 20 may be, for example, a two-piece structure. That is, cap assembly 20 may include a sleeve 22 and a cap 24. Sleeve 22 may have a proximal end 26 coupled to shaft 12 and a distal end 28 coupled to cap 24. For example, proximal end 26 may be coupled to shaft 12 along, near, or adjacent distal end 14, while distal end 28 may be coupled to a proximal end 30 of cap 24. Sleeve 22 may include a central bore (not shown) extending therethrough. The bore of sleeve 22 may be configured to receive a portion of shaft 12 and a portion of cap 24 therein. That is, the bore of sleeve 22 may grip, secure to, hold, or otherwise couple to each of shaft 12 and cap 24. For example, at least a portion of sleeve 22 may comprise an elastomeric material that tightly, closely, or snuggly, receives shaft 12 and cap 24 therein. That is, due to the elastomeric material of sleeve 22, a portion of sleeve 22 may be stretched about an exterior surface of shaft 12, while another portion of sleeve 22 may be stretched about an exterior surface of cap 24, so as to securely couple sleeve 22 to shaft 12 and cap 24.

As shown in FIG. 1, sleeve 22 may include a varied diameter along its length. That is, proximal end 26 of sleeve 22 may have a first radial dimension (e.g., size, diameter, etc.) while distal end 28 of sleeve 22 may have a second radial dimension (e.g., size, diameter, etc.) different (e.g., larger) than the first radial dimension. In this manner, sleeve 22 may couple shaft 12 having a radial dimension smaller than a radial dimension of cap 24 to one another. In other words, sleeve 22 may be a transition portion between shaft 12 and cap 24. Sleeve 22 may include one or more baffles 32. Baffles 32 may enhance the structural integrity of sleeve 22 to prevent the elastomeric material of sleeve 22 from becoming overly stretched out. Baffles may have any appropriate size, shape, and may be arranged in any appropriate manner (e.g., equidistantly or non-equidistantly) about the external circumferential surface of sleeve 22 without departing from the scope of this disclosure.

Sleeve 22 may further include a sleeve channel 34 and a pair of arms 36. Sleeve channel 34 may include a recess or groove extending along the exterior surface of sleeve 22. In such a manner, sleeve channel 34 may receive, accept, hold therein and/or guide a sheath 52 of a medical tool 50 therethrough. Arms 36 may have a first end coupled to sleeve 22 in any appropriate manner such as, for example, glued, welded, fastened, strapped, or any other such mechanical fastening (e.g., screws, pins, etc.). Alternatively, the first end of each of arms 36 may be monolithically formed as a one-piece construction with sleeve 22 via any appropriate process (e.g., molding). Additionally, each of arms 36 may have a second end, opposite the first end, which is free or otherwise uncoupled from sleeve 22. One or both of arms 36 may be semi-rigid, conformable, flexible, or resilient such that one or both arms 36 may pivot, flex, or deflect away from the other of arms 36 to increase a distance between arms 36 upon the application of a force. Arms 36 may define opposed mating surfaces between which sheath 52 of medical tool 50 may be securely held. In some arrangements, arms 36 may have a curved or arcuate profile or shape.

Cap 24 may comprise a transparent material (e.g., polycarbonate) so as to allow visualization by a medical professional therethrough. As shown in FIG. 1, cap 24 may have a circular cross-sectional shape. As such, cap 24 may be generally tubular and may define a central lumen 25. However, other arrangements are within the scope of this disclosure. For instance, cap 24 may have a partial circumferential (e.g., semi-circular) cross-sectional shape. Further, as shown in FIG. 1, cap 24 may have a varied outer surface size, dimension, or diameter along its length. For example, proximal end 30 of cap 24 may have a first outer dimension (e.g., size, diameter, etc.) while a distal end 38 of cap 24 may have a second outer dimension (e.g., size, diameter, etc.) different (e.g., smaller) than the first outer dimension. For example, cap 24 may have an outer tapering surface in the distal direction. Such tapering may facilitate deployment of medical tool 50 along a desired angle, as will be described in further detail below.

As shown, cap 24 may have a drain hole 40 extending therethrough. That is, drain hole 40 may extend through the thickness of a side wall of cap 24 to enable a medical professional to evacuate, clear, or otherwise remove blood or other such visual obstructions from central lumen 25 through drain hole 40. That is, a medical professional may deliver an appropriate irrigation fluid (not shown) through endoscope 10, into cap assembly 20, and out through drain hole 40 without being required to invert or otherwise reposition endoscope 10 to allow removal of obstructions via gravity. In addition, cap 24 may define a cap channel 42 along an external surface thereof. Cap channel 42 may include a recess or groove extending along the outer surface of cap 24. In such a manner, cap channel 42 may receive, accept, hold therein and/or guide medical tool 50 along cap 24. As shown, cap channel 42 may be aligned or otherwise be an extension or continuation of sleeve channel 34. That is, sleeve channel 34 and cap channel 42 may arranged such that medical tool 50 may be received along the exterior surface of cap assembly 20 from sleeve 22 to cap 24. Cap channel 42 may have a varied depth dimension. For example, as shown in FIG. 1, a portion of cap channel 42 adjacent proximal end 30 of cap 24 may be deeper than a depth of cap channel 42 positioned closer to distal end 38 of cap 24. The varied depth of cap channel 42 may facilitate deployment of medical tool 50 along a desired angle, as will be described in further detail below.

Cap 24 may further include an engagement feature. For example, as shown in the arrangement of FIG. 1, cap 24 may comprise a protrusion, extension, or button 44. Button 44, as shown, may extend radially outwardly of the exterior circumferential surface of cap 24. In addition, button 44 may have a general mushroom-shaped structure including a distal head portion 46 and a proximal post 48 located between an outer surface of cap 24 and head 46. Head 46 may be enlarged relative to post 48. In addition, head portion 46 may be rounded or otherwise atraumatic to surrounding tissue of the subject. As shown, head portion 46 may be circular. However, other shapes are within the scope of this disclosure, including, but not limited to, oval, and irregular curved shapes. As shown in FIG. 1, medical tool 50 may comprise a snare having a snare sheath 52 and a snare loop 54. In use, as shown in FIG. 1, medical tool 50 may be positioned alongside (e.g., extending along an exterior surface of) shaft 12, within sleeve channel 34, arms 36, and cap channel 42, while snare loop 54 of medical tool 50 may be extended distally of snare sheath 52 and closed around button 44. That is, snare loop 54 may be tightened about post 48 between the exterior surface of cap 24 and head portion 46. In such a manner, medical tool 50 may be securely held in place alongside endoscope 10 during insertion of endoscope 10 and into the body of the subject.

Figure 2A:
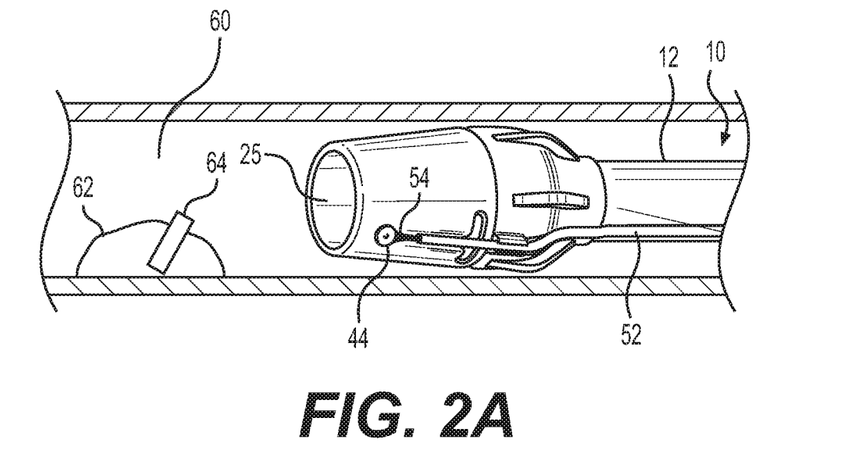
FIGS. 2A-2C illustrate a method for using the cap assembly to position the medical tool of FIG. 1.
Figure 2B:
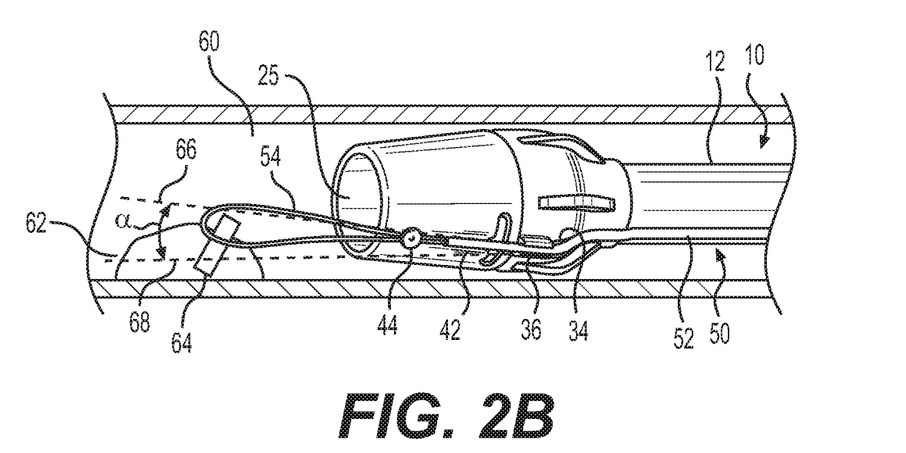
Figure 2C:
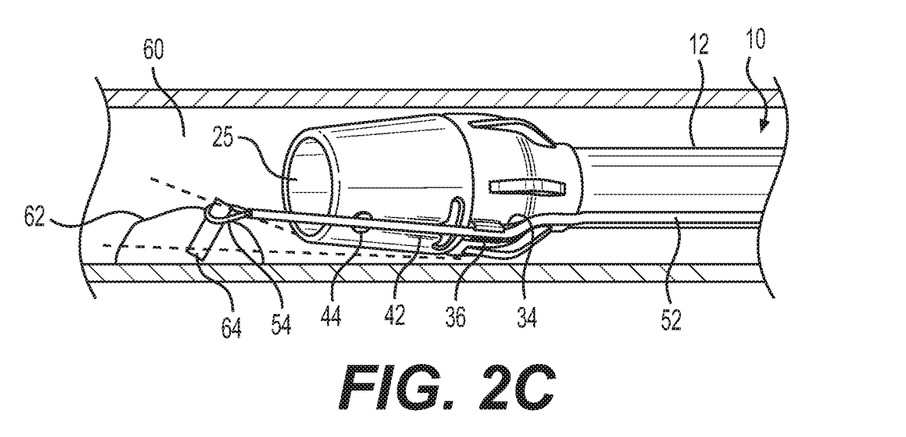

FIGS. 2A-2C illustrate various views of endoscope 10 and medical tool 50 during use. For example, as shown in FIG. 2A, endoscope 10 may be delivered through one or more lumens, organs, or other such passages 60 (e.g., the GI tract) of a subject. Upon delivery of endoscope 10 to a location within passage 60, one or more tools (e.g., needles, not shown) may be delivered through working channel 16 of endoscope 10, as necessary, to lift a lesion 62 or other such tissue abnormality from a surface of passage 60. Once lifted or otherwise sufficiently protruding into passage 60, an additional tool (e.g., a knife or blade, not shown) may be delivered through working channel 16 of endoscope 10 to at least partially resect lesion 62. If the medical professional determines that the partially resected lesion 62 obscures, blocks, or otherwise impedes his or her ability to visualize lesion 62 or other tissue layers (e.g., the submucosa), he or she may attach a hemoclip 64 through any appropriate means onto the partially-resected lesion 62, as is known.

Next, as shown in FIG. 2B, the medical professional may open or otherwise expand snare loop 54. For example, the medical professional may distally advance snare loop 54 relative to snare sheath 52 allowing snare loop 54 to form an expanded arrangement, as shown in FIG. 2B, and as is known in the art. For example, snare loop 54 may be comprised of a flexible, outwardly biased material such that upon extension of snare loop 54 distally of snare sheath 52, snare loop 54 may be free to expand. Snare loop 54 may also be comprised of any appropriate shape memory alloy materials such as, for example, Nitinol. Once opened and/or expanded, snare loop 54 may disengage from button 44 and may be extended distally of cap assembly 20 and be positioned about hemoclip 64. As shown in FIG. 2B, due to the tapered arrangement of cap 24 and the varied depth of cap channel 42, extension of snare loop 54 may occur along an axis 66 angled (e.g., along an angle α) relative to an axis 68 extending along an axis parallel with a central longitudinal axis 69 (see, e.g., FIG. 3A) of central lumen 25. That is, the take-off or deployment angle α of medical tool 50 may be adjusted by altering the degree of tapering of cap 24 or the degree of depth variation in cap channel 42. Due to angle α, when snare loop 54 is positioned distally of cap 24, it is easily and readily visible to a medical professional via endoscope 10. That is, once deployed along angle α, snare loop 54 remains in the line of sight of the medical professional to further aid proper positioning. In some arrangements, snare loop 54 may be positioned circumferentially about hemoclip 64 without the need for an additional tool. Optionally, however, a forceps or grasper device (not shown) may be delivered through working channel 16 of endoscope 10 and through central channel 25 of cap 24. The forceps may be used to grasp snare loop 54 and position it about hemoclip 64, if necessary.

In either arrangement, once snare loop 54 is positioned about hemoclip 64, the medical professional may close or otherwise tighten snare loop 54 about hemoclip 64, as shown in FIG. 2C. Closing or tightening snare loop 54 about hemoclip 64 may be accomplished by extending snare sheath 52 distally of button 44 to reduce the size of snare loop 54. In so doing, snare sheath 52 may be pushed, advanced, or extended along cap assembly 20. For example, snare sheath 52 may be guided by sleeve channel 34, arms 36, and cap channel 42 towards the position shown in FIG. 2C. Closing of snare loop 54 about hemoclip may enable manipulation of the partially-resected lesion 62 through manipulation of medical tool 50. For instance, once engaged with hemoclip 64, the medical professional may advance, retract, rotate, lift, depress, or otherwise adjust an orientation or positioning of partially-resected lesion 62 to facilitate visual observation of lesion 62 and/or other tissue structures.

Figure 3A:
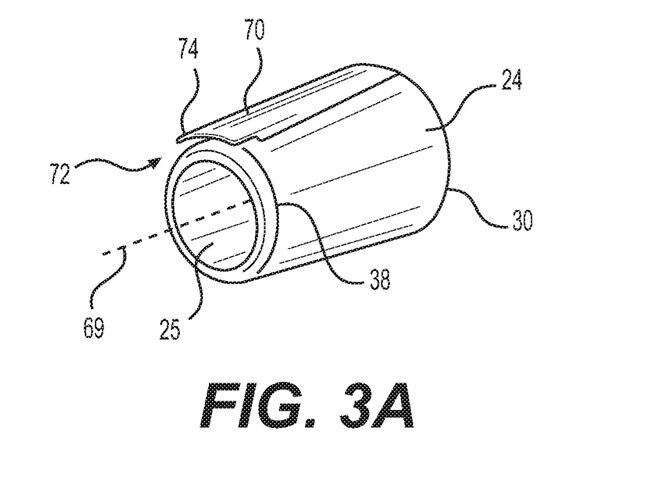
FIGS. 3A-3F illustrate further exemplary arrangements of a cap assembly according to aspects of the disclosure.
Figure 3B:
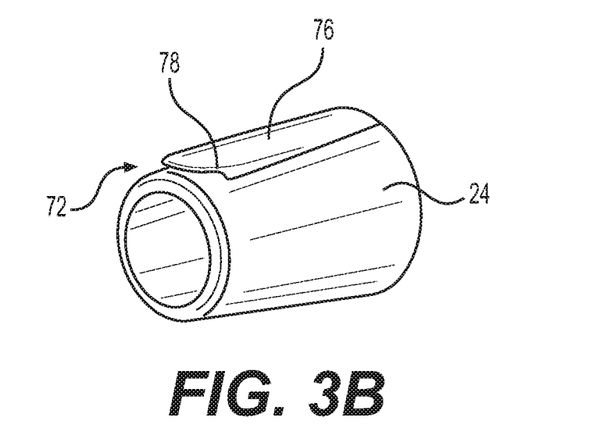

FIGS. 3A-3F illustrate various alternative arrangements for securing snare loop 54 to cap 24 during delivery of endoscope 10 into the subject. For example, as shown in FIG. 3A, cap 24 may omit button 44. Rather, cap 24 may include a shroud or flap 70 on an external surface. Flap 70 may extend from proximal end 30 to distal end 38 of cap 24, generally parallel to axis 69 of central lumen 25. Due to the tapered arrangement of cap 24, cap 24 and flap 70 gradually diverge from one another towards distal end 38 of cap 24 so as to define a space or gap 72. As shown in FIG. 3A, flap 70 may have a distal-most end 74 terminating in a plane generally parallel with or the same plane as a distal-most end face of cap 24. Optionally, however, a shroud or flap 76 (similar in construction and function to flap 70) may have a rounded, curved, or otherwise atraumatic distal-most end 78, as shown in FIG. 3B. In either such arrangement, snare loop 54 may be positioned within gap 72, between the exterior surface of cap 24 and an interior surface of flap 70 or flap 76. In such a manner, snare loop 54 is securely held in place alongside endoscope 10 during insertion of endoscope 10 and into the body of the subject.

Figure 3C:
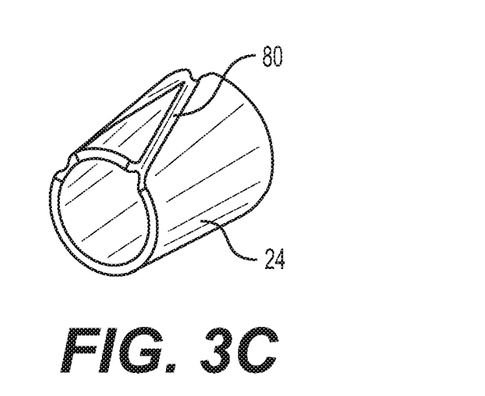

In another arrangement, as shown in FIG. 3C, a channel 80 may be positioned along cap 24. For example, channel 80 may be v-shaped and extend into the thickness of cap 24. In use, snare loop 54 may be positioned within channel 80 and tightened so as to be secured therein for insertion of endoscope 10 into the body of the subject. Although not shown in FIGS. 3A-3C, sleeve 22 (FIG. 1) may be arranged so as to couple cap 24 to endoscope 10, as described above.

Figure 3D:
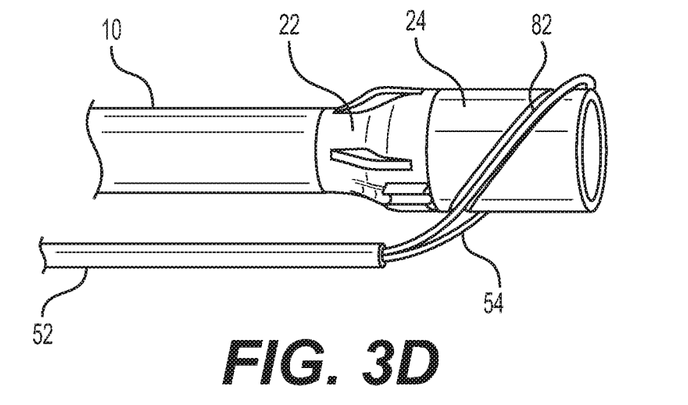
Figure 3E:
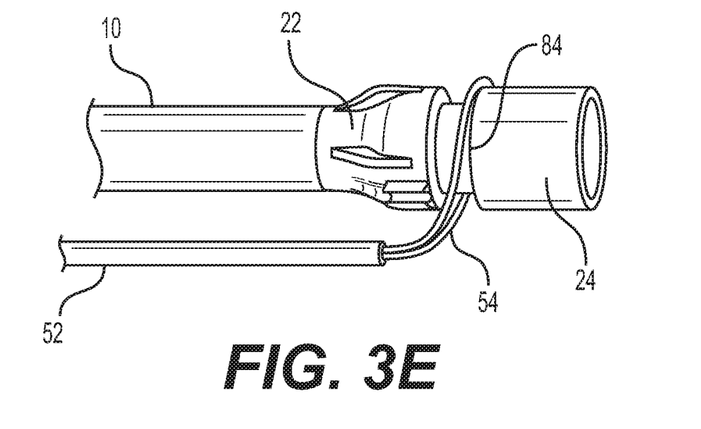
Figure 3F:
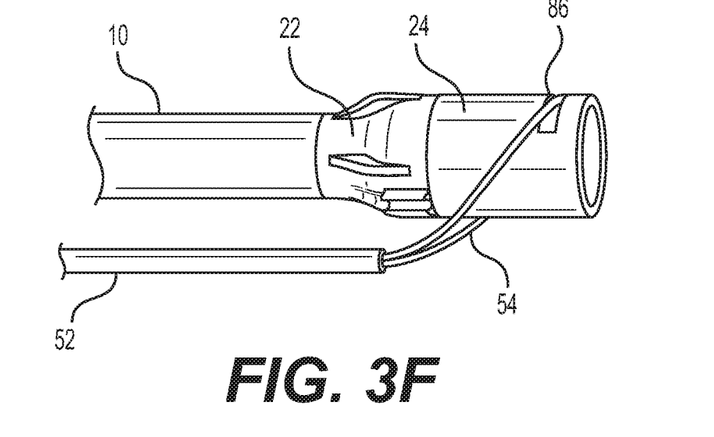

FIGS. 3D-3F each illustrate an exemplary cap 24 having a channel positioned along cap 24. For instance, cap 24 may have an angled channel 82 (FIG. 3D), a full (e.g., 360°) circumferential channel 84 (FIG. 3E), or a partial circumferential (e.g., less than 360°) channel 86 (FIG. 3F) thereon. The degree of angle of angled channel 82 may be selected upon a desired deployment angle α of snare loop 54. Each of channels 82, 84, and 86 may be function in a manner similar to channel 80, described above. For example, snare loop 54 may be inserted within one of channels 82, 84, or 86, and then tightened to securely couple snare loop 54 to cap 24 for insertion of endoscope 10 into the body of the subject. While each of FIGS. 3D-3F illustrate snare sheath 52 uncoupled from arms 36, such a depiction is merely to facilitate visualization of components of sleeve 22. In use, however, snare sheath 52 would be received within arms 36, as discussed above in connection with FIGS. 1-2C.

Figure 4:
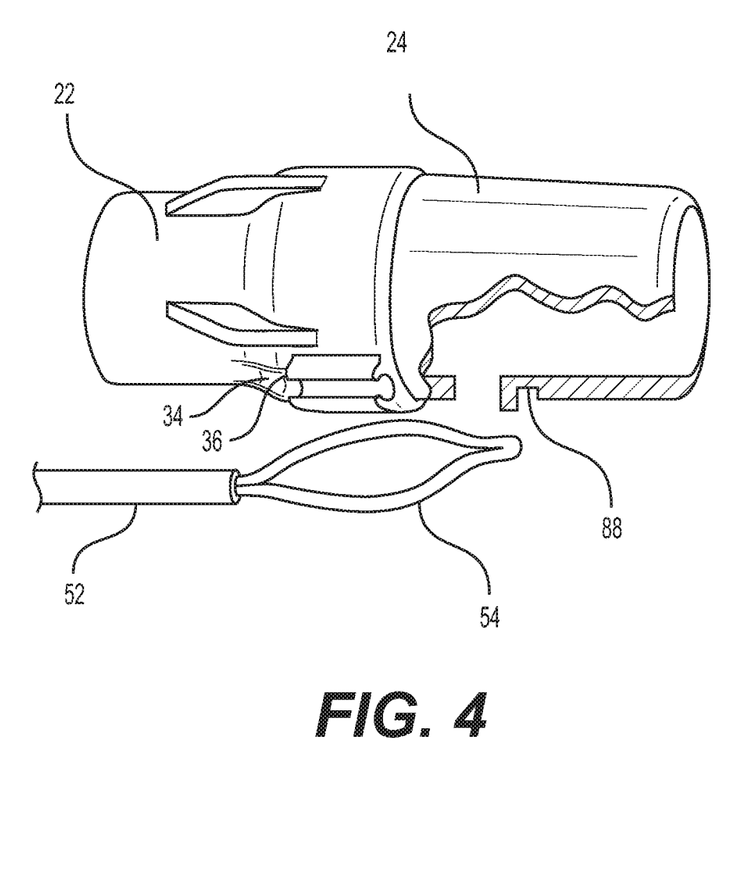
FIG. 4 illustrates another exemplary arrangement of a cap assembly according to aspects of the disclosure.
Figure 5A:
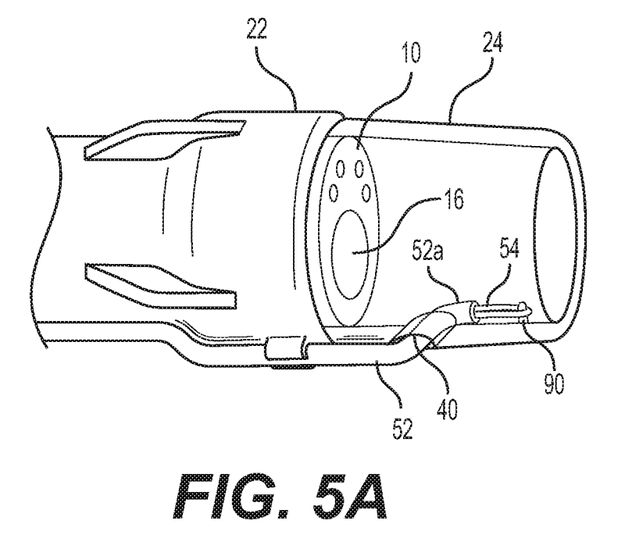
FIGS. 5A and 5B illustrate side and front views, respectively, of an additional cap assembly according to aspects of the disclosure.
Figure 5B:
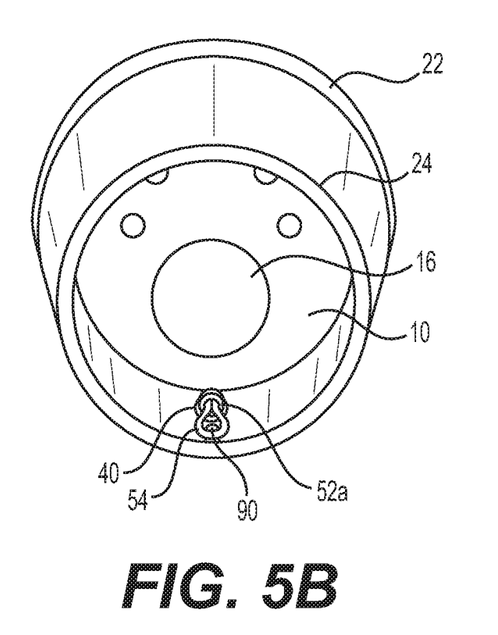

FIG. 4 illustrates a partial cut-away view of a still further arrangement of cap 24. As shown, cap 24 may omit button 44. Rather, cap 24 may include an extension, protrusion, peg, elbow, or hook 88 on an external surface of cap 24. In use, snare loop 54 may be positioned about hook 88 and tightened so as to be secured thereto for insertion of endoscope 10 into the body of the subject. While the arrangement of FIG. 4 illustrates an engagement feature, e.g., hook 88 on an external surface of cap 24, in some arrangements, an engagement feature may be positioned along an interior surface of cap 24. For example, as shown FIGS. 5A and 5B, cap 24 may include a button, hook, protrusion, extension, or cleat 90 on an internal surface of cap 24. In use, snare loop 54 may be positioned about cleat 90 and tightened so as to be secured thereto for insertion of endoscope 10 into the body of the subject. In addition, as shown, a distal-most portion 52a of the snare sheath 52 may be received through drain hole 40. That is, in order to couple snare loop 54 to cleat 90, distal-most portion 52a of snare sheath 52 may be inserted through drain hole 40 to position snare loop 54 internally of cap 24. Then, snare loop 54 may be extended distally of distal-most portion 52a of snare sheath 52 and positioned and tightened around cleat 90. In such a fashion, during insertion of endoscope 10 into the body of the subject, distal-most portion 52a is positioned within cap 24 and as such, is atraumatic to tissue in the body of the subject. It should be understood that while distal-most portion 52a has been depicted and described as extending through drain hole 40, the disclosure is not so limited. Rather, an additional hole (not shown), discrete from drain hole 40, may be disposed through cap 24 for receipt of distal-most portion 52a therethrough.

Figure 6A:
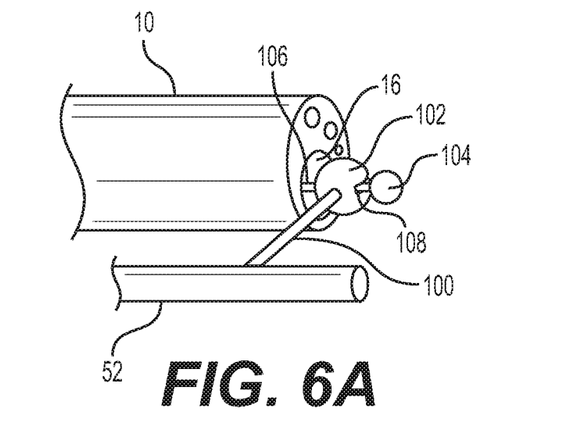
FIGS. 6A-6C illustrate an additional method of securing the medical tool of FIG. 1 to the endoscope of FIG. 1, according to aspects of the disclosure.
Figure 6B:
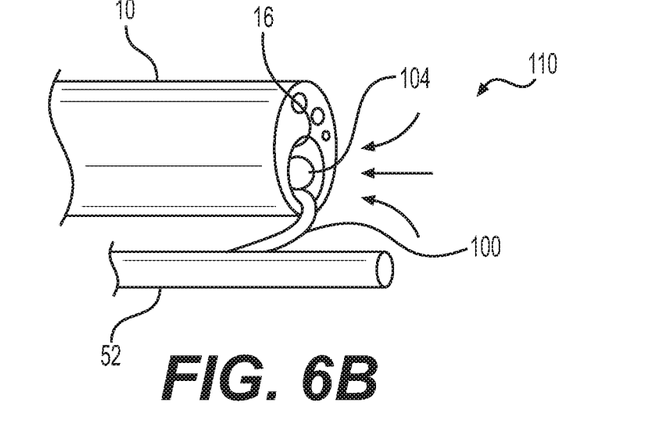
Figure 6C:
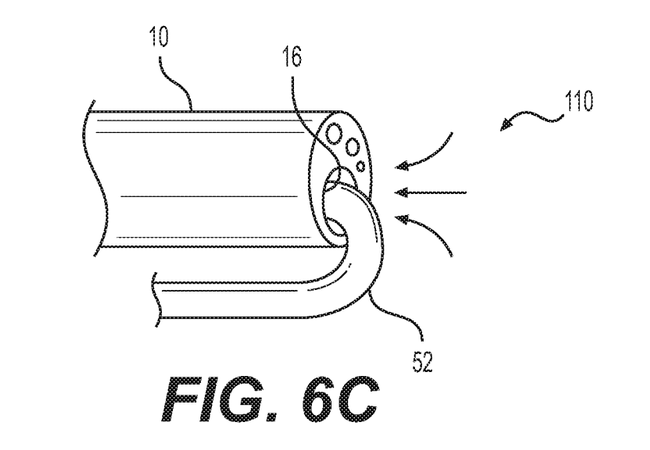

FIGS. 6A-6C illustrate a still further arrangement, in which cap assembly 20 may be omitted, as shown. It should be understood that while cap assembly 20 is not depicted in this arrangement, cap assembly 20 may optionally be included according to the preference of the medical professional and/or the requirements of the medical procedure. As shown in FIG. 6A, snare sheath 52 may include a coupling mechanism 100. In some arrangements, coupling mechanism 100 may be directly coupled to or monolithically formed (e.g., molded) with snare sheath 52. In some arrangements, however, coupling mechanism 100 may be coupled to or monolithically formed with snare loop 54. Coupling mechanism 100 may include a shaft or wire extending from snare sheath 52 towards a clutch mechanism 102. As shown, clutch mechanism 102 may include a ball-shaped grasper with a groove 108 therein. In other arrangements, clutch mechanism 102 may not be ball-shaped. Rather, clutch mechanism 102 may be ovular, irregular, or any other shape sized or arranged to be received within working channel 16 of endoscope 10, as will be described in further detail below. Clutch mechanism 102 may be made of a flexible rubber material or the like. Groove 108 may be removably (e.g., detachably) coupled to a shaft 106 of a tool, such as a ball cutter 104 via a transition fit. As such, shaft 106 of ball cutter 104 may be held precisely, yet not so tightly that it cannot be removed therefrom. As such, groove 108 may retain shaft 106 therein until a force (e.g., a push or pull force) is applied to snare sheath 52 while ball cutter 104 is positioned in FIG. 6A. That is, groove 108 may wrap around, be received therein, or otherwise be secured to shaft 106, as shown in FIG. 6A. Additionally, due to the enlarged shape or structure of ball cutter 104, ball cutter 104 may prevent inadvertent dislodgement of shaft 106 from groove 108. While ball cutter 104 is depicted and described, the disclosure is not limited. Rather, clutch mechanism 102 may be selectively coupled and uncoupled from a shaft of any appropriate tool and or sheath such as, e.g., laser fibers, baskets, guide-wires, scissors, etc.

In order to secure snare sheath 52 to endoscope 10 for delivery into the body of a subject, a medical professional may retract shaft 106 of ball cutter 104 proximally into working channel 16 of endoscope 10, as shown in FIG. 6B. Optionally, clutch mechanism 102 may be held within the working channel 16 of the endoscope without the use of a tool such as ball cutter 104. That is, a user may align or position clutch mechanism 102 in close proximity with working channel 16, and then, may actuate a vacuum source (not shown) so as to create a suction force 110 to retain snare sheath 52, as shown in FIG. 6B. In such a manner, snare sheath 52 may be positioned alongside endoscope 10 solely due to the interaction between clutch mechanism 102 and the suction force, and without the use of ball cutter 104.

Optionally, the medical professional may continue actuation of the vacuum source to pull, or otherwise draw snare sheath 52 into working channel 16 of endoscope 10. In doing so, snare sheath 52 may bend and/or fold around a distal-most end face of endoscope 10. In arrangements in which cap assembly 20 is used, snare sheath 52 may bend or fold around a distal-most end face of cap 24 and into central channel 25.

Once snare sheath 52 is retained either alongside the endoscope 10 as shown in FIG. 6B and/or once clutch mechanism 102 is positioned within working channel 16 and/or central channel 25, endoscope 10 may be inserted into the body of the subject. When it is desired to position snare loop 54 (not shown in FIGS. 6A-6C) about a hemoclip, suction force 110 may be removed, and the medical professional may distally-advance shaft 106 of ball cutter 104 to guide snare sheath 54 towards the hemoclip. Once in position, snare loop 54 may be positioned and tightened around hemoclip and may dislodge or eject shaft 106 from groove 108.

Figure 7A:
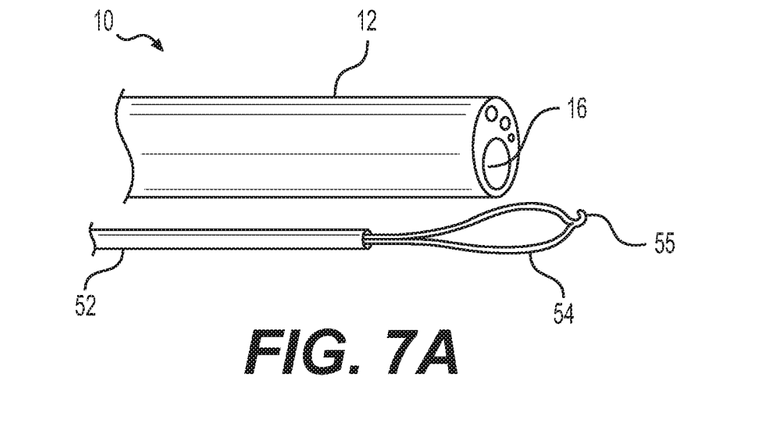
FIGS. 7A-7C illustrate additional arrangements of the endoscope and medical tool of FIG. 1, according to aspects of the disclosure.
Figure 7B:
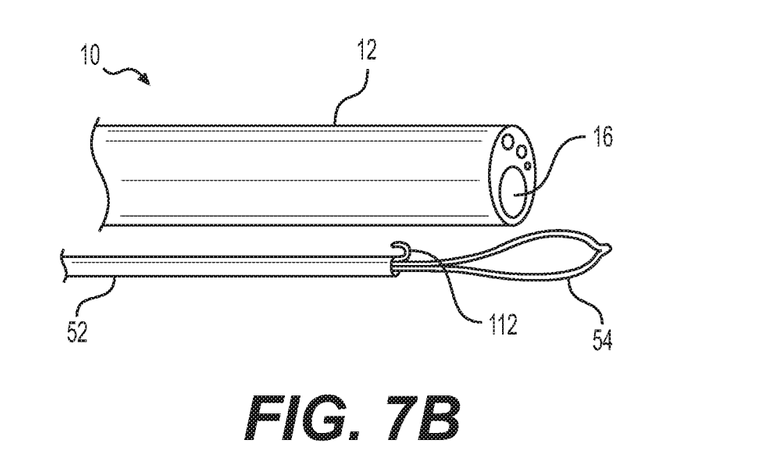
Figure 7C:
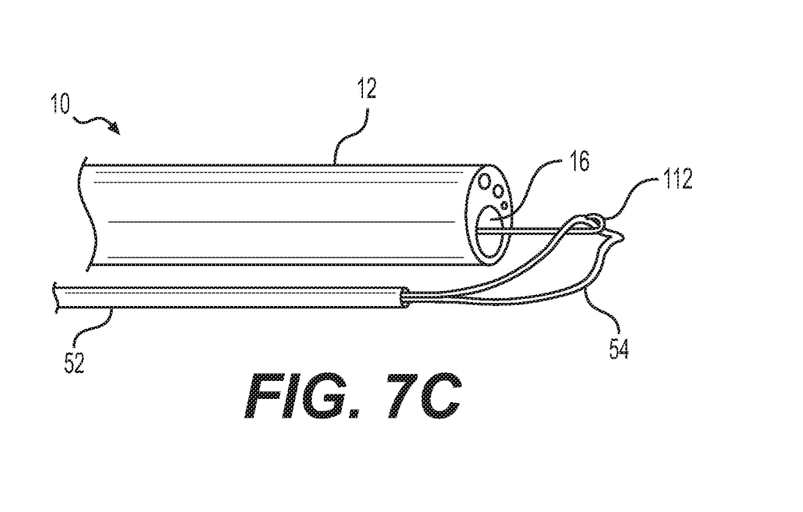

FIGS. 7A-7C illustrate additional exemplary arrangements in which cap assembly 20 may be omitted, as shown. It should be understood that while cap assembly 20 is not depicted in these arrangements, cap assembly 20 may optionally be included according to the preference of the medical professional and/or the requirements of the medical procedure. As shown in FIG. 7A, snare loop 54 may include an engagement device such as, for example, a hook 55. Hook 55 may be coupled to or monolithically formed with snare loop 54. In either manner, hook 55 may hook onto or around a distal-most end face of endoscope 10. In arrangements in which a cap assembly 20 is used, hook 55 may hook onto or around a distal-most end face of cap 24. In such a manner, hook 55 may secure snare loop 54 in place relative to endoscope 10 for delivery into the body of the subject. Alternatively, hook 55 may be separate and discrete from snare loop 54. For example, as shown in FIGS. 7B and 7C, a separate hook tool 112 may be used to maintain snare loop 54 relative to endoscope 10. As shown, hook tool 112 may be delivered through snare sheath 52 alongside snare loop 54 (FIG. 7B) or may be delivered through a channel (e.g., working channel 16) of endoscope 10 (FIG. 7C). In either arrangement, hook tool 112 may be positioned about snare loop 54 relative to endoscope 10.

Figure 8:
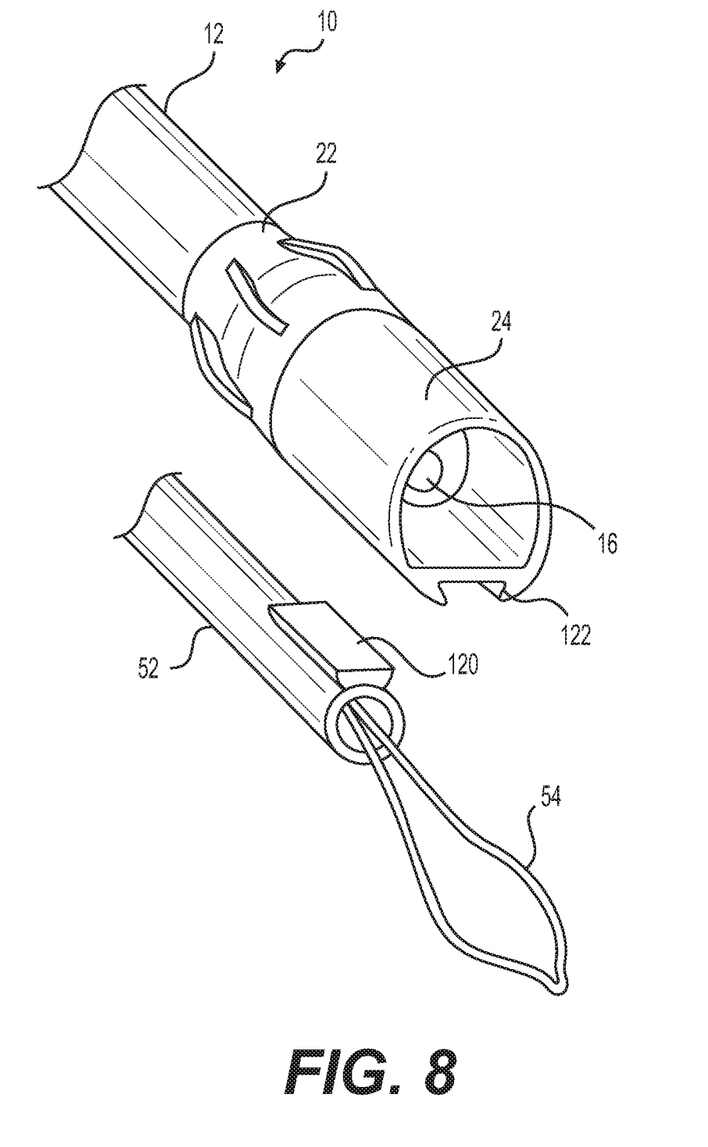
FIG. 8 illustrates an additional cap assembly and medical tool, according to aspects of the disclosure.

FIG. 8 illustrates an exploded view of a still further exemplary arrangement in which snare sheath 52 include a key feature 120 configured to mate or otherwise correspond in shape with a recess or channel 122 along an exterior surface of cap 24. For example, key feature 120 and channel 122 may be in the form of a dove-tail arrangement. Key feature 120 may have any appropriate cross-sectional shape such as, e.g., a trapezoid, as shown in FIG. 8. Additional cross-sectional shapes may include, a semicircle, triangular, etc. In use, key feature 120 may be inserted into or otherwise cooperate with channel 122 to retain snare sheath 52 relative to endoscope 10.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

We claim:

1. A cap for a medical device, the cap comprising:
a wall defining a central lumen and having an outer circumferential surface wherein the lumen is radially inward of the wall and the outer circumferential surface; and
a feature disposed on and protruding outwardly from the outer circumferential surface of the cap, wherein a distalmost end of the feature is fixed proximal of a distalmost end of the cap, and wherein the feature is configured to receive a snare loop of a medical device about the feature, such that, in at least one configuration of the snare loop, an entirety of the snare loop is positioned to one side of a central longitudinal axis of the central lumen, wherein the wall includes a cap channel distinct from the central lumen, and extending longitudinally along the outer circumferential surface.

2. The cap of claim 1, wherein the cap channel is configured to receive a sheath of the medical device.

3. The cap of claim 2, wherein at least a portion of the cap channel is open such that the sheath is only partially circumferentially surrounded by the cap channel.

4. The cap of claim 1, further comprising an elastomeric sleeve.

5. The cap of claim 4, wherein the sleeve includes a sleeve channel extending along a length of the sleeve, wherein the sleeve channel is aligned with the cap channel.

6. The cap of claim 5, wherein the sleeve channel extends along an outer circumferential surface of the sleeve.

7. The cap of claim 4, wherein the sleeve further includes a pair of arms extending from an outer circumferential surface of the sleeve, and wherein the pair of arms are configured to receive a sheath of the medical device.

8. The cap of claim 1, wherein the feature includes a post and a head.

9. A cap for a medical device, the cap comprising:
 a continuous wall defining a central lumen, having an outer circumferential surface, and a distal end completely surrounding the central lumen; and
 a feature disposed on and protruding outwardly from the outer circumferential surface of the cap, proximal of a distalmost end of the cap, and wherein the feature is configured to receive a snare loop of a medical device about the feature, such that, in at least one configuration of the snare loop, an entirety of the snare loop is positioned to one side of a central longitudinal axis of the central lumen, wherein the wall includes a cap channel radially outside of the central lumen.

10. The cap of claim 9, wherein the cap channel is configured to receive a sheath of the medical device.

11. The cap of claim 10, wherein at least a portion of the cap channel is open such that the sheath is only partially circumferentially surrounded by the cap channel.

12. The cap of claim 9, wherein the cap channel extends along the outer circumferential surface.

13. The cap of claim 9, further comprising an elastomeric sleeve.

14. The cap of claim 13, wherein the sleeve includes a sleeve channel extending along a length of the sleeve, wherein the sleeve channel is aligned with the cap channel.

15. The cap of claim 14, wherein the sleeve channel extends along an outer circumferential surface of the sleeve.

16. The cap of claim 13, wherein the sleeve further includes a pair of arms extending from an outer circumferential surface of the sleeve, and wherein the pair of arms are configured to receive a sheath of the medical device.

17. A cap for a medical device, the cap comprising:
 a wall defining a central lumen and having an outer circumferential surface;
 an elastomeric sleeve; and
 a feature disposed on and protruding outwardly from the outer circumferential surface of the cap, proximal of a distalmost end of the cap, and wherein the feature is configured to receive a snare loop of a medical device about the feature, such that, in at least one configuration of the snare loop, an entirety of the snare loop is positioned to one side of a central longitudinal axis of the central lumen, wherein the wall includes a cap channel extending along a length of the outer circumferential surface, wherein the cap channel is configured to receive a sheath of the medical device, and wherein at least a portion of the cap channel is open such that the sheath is only partially circumferentially surrounded by the cap channel.

18. The cap of claim 17, wherein the sleeve includes a sleeve channel extending along a length of the sleeve, wherein the sleeve channel is aligned with the cap channel.

19. The cap of claim 18, wherein the sleeve channel extends along an outer circumferential surface of the sleeve.

20. The cap of claim 17, wherein the sleeve further includes a pair of arms extending from an outer circumferential surface of the sleeve, and wherein the pair of arms are configured to receive the sheath of the medical device.

* * * * *